(12) United States Patent
Linari

(10) Patent No.: US 12,307,846 B2
(45) Date of Patent: May 20, 2025

(54) SYSTEM AND METHOD FOR MONITORING THE CONDITIONS AND MOVEMENTS OF A USER WITHIN AN AREA OF INTEREST

(71) Applicant: Linari Medical S.r.l., Pisa (IT)

(72) Inventor: Stefano Linari, Pisa (IT)

(73) Assignee: Linari Medical S.r.l., Pisa (IT)

( * ) Notice: Subject to any disclaimer, the term of this patent is extended or adjusted under 35 U.S.C. 154(b) by 77 days.

(21) Appl. No.: 18/463,567

(22) Filed: Sep. 8, 2023

(65) Prior Publication Data

US 2025/0087041 A1    Mar. 13, 2025

(51) Int. Cl.
*A61B 5/01* (2006.01)
*A61B 5/024* (2006.01)
(Continued)

(52) U.S. Cl.
CPC ............ *G07C 9/26* (2020.01); *A61B 5/02438* (2013.01); *G06K 7/10415* (2013.01);
(Continued)

(58) Field of Classification Search
CPC ....... A61B 5/01; A61B 5/0008; A61B 5/6833; A61B 90/98; A61B 2562/0271; A61B 5/14552; A61B 5/1118; A61B 2562/164; A61B 2560/0412; A61B 2560/0271; A61B 2560/0214; A61B 5/0022; A61B 5/02438;
(Continued)

(56) References Cited

U.S. PATENT DOCUMENTS

2016/0188840 A1*  6/2016  Eramian ................. G07F 9/001
                                                     700/237
2016/0307437 A1*  10/2016  Stoffer ............... G06K 7/10346
                                (Continued)

FOREIGN PATENT DOCUMENTS

CN       111479225 A    7/2020
KR       102147505 B1   8/2020
KR       102304174 B1   9/2021

OTHER PUBLICATIONS

European Search Report and Written Opinion issued on Jul. 9, 2022, in corresponding Application No. 22160495, 10 pages.
(Continued)

*Primary Examiner* — Dionne Pendleton
(74) *Attorney, Agent, or Firm* — Maier & Maier, PLLC

(57) ABSTRACT

A system for monitoring conditions and movements of at least one user, including at least one adhesive monitoring device for skin application or monitoring patch applicable to the epidermis of a user to be monitored, the monitoring patch including an adhesive substrate for skin use has embedded or includes at least one sensor to detect a body temperature, a memory module to store data, and a transceiver module to absorb supplied electrical energy from an electromagnetic radiation received by an antenna; and a plurality of detecting devices, each of which is located in correspondence with at least an access gate to a sub-area of a plurality of sub-areas, the plurality of sub-areas defining a monitoring area. Each detecting device detects presence of the monitoring patch within a predetermined distance from the gate; activates a communication channel w; and transmits an identification code of the detecting device and a corresponding timestamp.

15 Claims, 11 Drawing Sheets

(51) Int. Cl.
   *A61B 90/90* (2016.01)
   *G01K 1/02* (2021.01)
   *G06K 7/10* (2006.01)
   *G06K 19/077* (2006.01)
   *G07C 9/00* (2020.01)
   *G07C 9/15* (2020.01)
   *G07C 9/26* (2020.01)
   *G07C 9/28* (2020.01)
   *H04W 4/38* (2018.01)

(52) U.S. Cl.
   CPC ... *G06K 19/07758* (2013.01); *G07C 9/00309* (2013.01); *G07C 9/15* (2020.01); *G07C 9/28* (2020.01); *H04W 4/38* (2018.02); *G07C 2009/00769* (2013.01); *G07C 2209/08* (2013.01); *G07C 2209/63* (2013.01)

(58) Field of Classification Search
   CPC ... A61B 5/7415; A61B 5/7425; A61B 5/7455; A61B 5/7465; G06K 7/10297; G06K 7/10415; G06K 19/0723; G06K 7/10366; G06K 19/0717; G06K 19/0728; G06K 19/07705; G06K 19/07758; G06K 7/10346; G06K 7/10356; G01K 13/20; G01K 1/02; G01K 1/024; G08B 25/10; G08B 13/1427; G08B 21/0227; G08B 21/0272; G08B 21/0286; G08B 21/0291; G08B 21/0294; G08B 25/016; H01Q 1/2208; H01Q 1/2225; H01Q 1/38; H01Q 15/08; H01Q 23/00; H01Q 7/00; H04B 1/38; H04B 5/45; H04B 5/70; H04B 5/79; H04B 5/263; H04B 5/266; H04W 4/38; H04W 4/80; H04W 52/0229; H04W 84/18; H04W 4/02; H04W 4/33; H04L 67/12; G16H 40/63; G16H 20/13; G16H 40/20; G16H 40/67; A61G 12/001; A61G 2203/46; A61G 2205/60; B62B 3/00; B62B 3/005; G01S 2201/01; G01S 5/02213; G01S 5/0295; G06F 1/1626; G06F 3/048; G06Q 10/08; G06Q 20/3278; G07F 9/001; G07F 9/002; H02J 2310/23; H02J 50/005; H02J 50/10; H02J 50/27

See application file for complete search history.

(56) References Cited

U.S. PATENT DOCUMENTS

| | | | |
|---|---|---|---|
| 2017/0091498 A1* | 3/2017 | Forster | G06K 7/10297 |
| 2020/0222261 A1* | 7/2020 | Ito | G06K 19/0728 |
| 2022/0101992 A1* | 3/2022 | Porter | A61B 5/01 |
| 2023/0245770 A1* | 8/2023 | Ayers | G16H 40/67 340/539.12 |

OTHER PUBLICATIONS

Italian Search Report issued on Nov. 11, 2021, in corresponding Application No. 202100005405, 13 pages.

* cited by examiner $R_C$

| Detector code | Timestamp | Temperature |
|---|---|---|
| $ID_{Ra}$ | $t_{Sa}$ | $TU_a$ |
| $ID_{Rb}$ | $t_{Sb}$ | $TU_b$ |
| $ID_{Rd}$ | $t_{Sd}$ | $TU_d$ |

Fig. 7

$R_{DBa}$

| Detector code | Timestamp | Temperature |
|---|---|---|
| ... | ... | ... |
| $ID_C$ | $t_{Sa}$ | $TU_a$ |
| ... | ... | ... |

| Patch code |
|---|
| ... |
| $ID_C$ |
| ... |

Fig. 10A $BL_T'$

| Patch code | Temperature |
|---|---|
| ... | ... |
| $ID_C$ | TU |
| ... | ... |

Fig. 10B $R_C$

| Patch code |
|---|
| ... |
| $ID_C$ |
| ... |

Fig. 11A

| Patch code | Prohibited area(s) |
|---|---|
| ... | ... |
| $ID_C$ | A2, A4 |
| ... | ... |

Fig. 11B

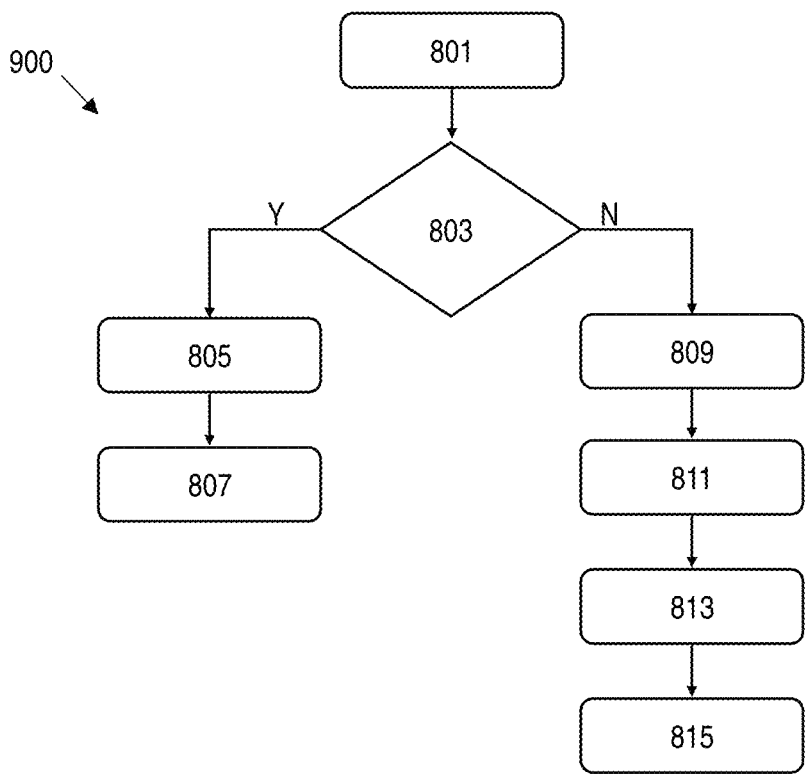
Fig. 17
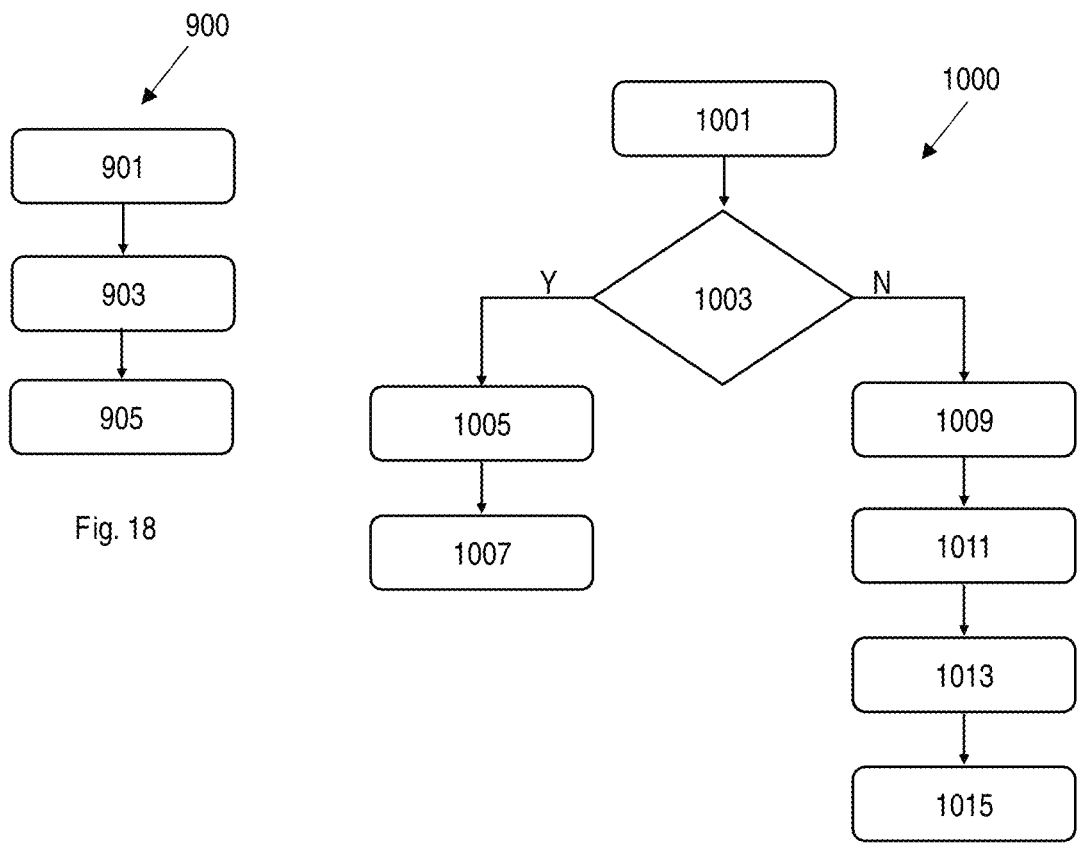
Fig. 18
Fig. 19

SYSTEM AND METHOD FOR MONITORING THE CONDITIONS AND MOVEMENTS OF A USER WITHIN AN AREA OF INTEREST

TECHNICAL FIELD

The present invention to the electronics sector. In detail, the invention relates to a system and related method for monitoring the conditions and movements of a user within an area. In greater detail, embodiments of the present invention relate to a system and method for recording movements, tracking at least one vital user parameter and/or identifying possible contacts between two or more users within an area of interest.

BACKGROUND

In the context of monitoring the movements in an area of interest, a variety of automated systems are known, ranging from systems that include electronic cards or keys to allow access to one or more areas to facial recognition-based systems that monitor and/or identify individuals crossing a monitored region.

However, such systems do not allow to check the condition of a user expressed through one or more vital parameters such as, for example, the body temperature of an individual in transit. In other words, such monitoring systems do not make it possible to identify a user who is potentially suffering from a disease, in particular an infectious disease, or, more generally, if his current condition is unsuitable for staying in a monitored area.

In an attempt to solve this problem, systems equipped with a sensor configured to detect the vital parameter of interest have been proposed, whereby users interact with this sensor to detect the vital parameter before accessing the monitored area.

However, such a system substantially lengthens the time it takes for a user to access or transit through the area of interest, as well as they do not allow the user to access data relating to his movements.

In addition, solutions based on the recognition of individuals and configured to detect the vital parameter of interest, in particular body temperature, through an analysis of the acquired graphic image and/or by acquiring a thermographic image in parallel to the graphic image have been proposed.

However, these systems are only effective if it is possible to capture a distinct image of each user, in particular the user's face, which can be difficult in crowded conditions as a correct detection requires framing one user at a time in the field of view of the camera capturing the images and/or in the periphery of this field of view.

None of the proposed systems allow for clear and reliable verification of which people a particular individual has come into contact with, greatly limiting the effectiveness of such systems in preventing the spread of infectious diseases among people accessing the monitored area.

In addition, US 2017/091498 describes a system for connecting a medical device with a smart device. The system comprises a medical device, a smart device, a package containing the medical device and an RFID device integrated into the package and associated with the medical device.

The method for connecting the medical device to a smart device includes removing the medical device from the package and applying it to a person, presenting the RFID device to the smart device, reading the RFID device with the smart device and using the information obtained from the RFID device to establish communications between the smart device and the medical device.

CN 111479225 describes a system comprising an electronic badge, a temperature control device, a UWB positioning system, a local host and a cloud server. The electronic badge is equipped with a shell, an RFID tag, a communication module and a microprocessor. The temperature monitoring device comprises a flexible patch and a Bluetooth module. The UWB positioning system comprises a plurality of UWB base stations. The local host is wirelessly connected to the electronic badge, the RFID reader and the UWB base stations via a wireless network. In addition, the host is connected to the cloud server. The body temperature of a user equipped with a badge and temperature control device is monitored, uploaded and made viewable in real time on the cloud server and an alarm is issued immediately when an abnormality occurs.

The system proposed in US 2017/091498 does not allow an individual's temperature and movements to be monitored at the same time, while the system described in CN 111479225 is particularly complex and expensive to implement in terms of cost and installation time. In addition, CN 111479225 is unsuitable for application in shielded environments or those requiring a particularly low level of electromagnetic radiations.

SUMMARY

It is an object of the present invention to overcome the drawbacks of the prior art.

In particular, it is an object of the present invention to provide a system and a related method configured to monitor a user within an area and at least one vital parameter of the user effectively and without affecting the speed of movement within the area of interest.

A further object of the present invention is to propose a system and a related method for identifying users crossing a gate to and from a monitored area or a sub-area thereof and detecting at least one vital parameter, preferably the temperature of the user, when passing through the gate.

A further object of the present invention is to present a system and a related method capable of securely recording movement data and data relating to the user's contingent conditions, while guaranteeing the confidentiality of the data of users moving in the area of interest.

A further object of the present invention is to present a system and a related method that allows the user to accurately and reliably reconstruct a path followed by a user within the area of interest and/or identify one or more other users with whom a specific user may have come into contact.

Another object of the present invention is to automatically and traceably restrict access to one or more sub-areas of a monitored area to a user with particular physiological conditions—for example, a body temperature higher than a threshold—and/or who does not have authorisation to access such sub-areas.

A further objects of the present invention is to provide a simple and robust system and related method, capable of operating even in the event of interruptions of data communication channels such as a wireless or wired network.

These and other objects of the present invention are achieved by a system incorporating the features of the annexed claims, which form an integral part of the present description.

According to a first aspect, the present invention is directed to a system for monitoring the conditions and movements of at least one user. The system comprises:

at least one adhesive monitoring device for skin application or monitoring patch, applicable to the epidermis of a user to be monitored, comprising an adhesive substrate for cutaneous use in which are embedded or to which are bound at least:
- a sensor configured to detect a body temperature of the user,
- a memory module, configured to store data, and
- a transceiver module which is configured to absorb supply electrical energy from an electromagnetic radiation received by means of an antenna, and a plurality of detecting devices, each of which is located in correspondence with at least a gate of a sub-area of a plurality of sub-areas, the plurality of sub-areas defining a monitoring area.

Advantageously, each detecting device is configured to:
- detect the presence of the least one monitoring patch within a predetermined distance from the gate;
- activate a communication channel with the at least one monitoring patch, and
- transmit an identification code of the at least one detecting device and a corresponding timestamp to the at least one monitoring patch detected within the predetermined distance.

In addition, the at least one monitoring patch is configured to
- transmit the user's body temperature data, and
- store in the memory module each detecting device identification code and each corresponding timestamp received.

The system thus constituted makes it possible to monitor the crossings of the gates in a completely transparent manner to the users moving within the area, at the same time allowing the acquisition of precise and reliable information on when and under what conditions each user has passed through a gate and, consequently, the sub-areas crossed and/or the time spent in each of these sub-areas. In addition, the monitoring patch allows the user to reconstruct his movements and his conditions at the time of each movement in a precise and complete manner, automatically and without specific intervention by the user.

In particular, the patch retains and allows to reconstruct when desired the path of the user, the crossed sub-areas and/or the time spent in each of these sub-areas.

Accordingly, the system can be implemented in a simple and particularly robust manner, as it does not necessarily require a control or information recording entity connected to the detecting devices, and where such a control or information recording entity is envisaged, the system is able to obtain and retain the information of interest even when a communication channel cannot be established with a remote control and/or information recording system or the communication channel is degraded.

Finally, retaining information about the user's path, the sub-areas crossed and/or the time spent in each of these sub-areas directly in the monitoring patch makes it possible to collect information about a user of interest in a simple and immediate way.

In one embodiment, the at least one monitoring patch is further configured to:
- transmit a patch identification code.

In addition, each detecting device is configured to:
- store the patch identification code of the at least one monitoring patch, the data of user's body temperature provided by the at least one monitoring patch and a timestamp associated with the reception of the patch identification code.

Thanks to this solution, each detecting device stores a unique triad of information each time a user crosses the gate. In addition, this solution allows to preserve the confidentiality of user data as the patch codes are not directly linked to the identity of a specific user.

In one embodiment, each one detecting device is configured to detect whether the body temperature data received from a monitoring patch is indicative of a body temperature measurement that is higher than a threshold value, and if the temperature measurement is greater than said threshold value:
- establish a communication channel with at least one remote entity,
- transmit an alert message, said alert message comprising the patch identification code of the monitoring patch that transmitted the body temperature data, and the corresponding timestamp.

The transmission of the alert message makes it possible to signal, substantially in real time, the presence and the approximate position of a user whose temperature is higher than the threshold value. This makes it possible to identify at an early stage the presence of users potentially affected by a disease and to intervene promptly to limit the possibility of the spread of an infectious disease among users within the area of interest.

In one embodiment, the system comprises a remote management unit, and a plurality of monitoring patches. In particular, each monitoring patch is applied to a respective user to be monitored.

In addition, each detecting device that detects a monitoring patch is configured to transmit to said at least remote management entity:
- the identification code of the detecting device,
- a plurality of patch identification codes received,
- a plurality of timestamps each associated with the reception of a patch identification code, and
- a plurality of body temperature measurements of the user each received together with a patch identification code.

Preferably, the remote management entity is configured to store a detector log for each detecting device. The detector log comprises the identification code of each monitoring patch detected by the detecting device, the corresponding timestamp and the corresponding data of user's body temperature transmitted by the monitoring patch.

The remote management entity allows keeping a centralised record of users passing through the gates in the sub-areas of the area of interest. This makes it possible, on the one hand, to reduce the hardware requirements of the detecting devices and, on the other, to efficiently combine the data provided by all the detecting devices of the system.

In one embodiment, the monitoring patch is configured to:
- transmit each identification code and the corresponding timestamp received from each detecting device stored in the memory module.

In addition, the detecting device that detects the at least one monitoring patch is configured to:
- include in said alert message each identification code and the corresponding timestamp received from each detecting device stored in the memory module.

This allows accurate information about a path taken by the user within the monitoring area to be obtained automatically and in a timely manner.

In one embodiment, the system also comprises a user device configured to:

activate a communication channel with the at least one monitoring patch to receive a patch identification code transmitted by the at least one monitoring patch, associate said patch identification code with a file representative of a user's certificate, preferably encrypted, and establish a communication channel with a remote entity, and transmit the patch identification code and the file representative of the certificate in digital format of the user associated.

Alternatively, the user device, after receiving the patch identification code, is configured to:

establish a communication channel with a remote entity, and transmit the patch identification code.

In this case, it is the remote entity that associates the patch identification code with the file representative of the user's certificate.

The monitoring patch can therefore be used as a device for recognising and checking the possession of a certificate in digital format—for example, a vaccination or prophylaxis certificate such as the so-called EU Digital COVID Certificate—by a user. Consequently, it is possible to check the possession of a certificate in digital format in an immediate and completely transparent way to the user, without the need for image capture tools such as cameras or video cameras.

In one embodiment, the system comprises a reader device configured to activate a communication channel with the monitoring patch. The monitoring patch is configured to transmit each identification code and the corresponding timestamps received from each detecting device stored in the memory module of the monitoring patch.

The reader device allows secure acquisition of the data recorded by the monitoring patch. As a result, it is possible to automatically and accurately reconstruct the path of a monitoring patch and, therefore, of the user wearing such a monitoring patch within the area of interest, the time spent in the sub-areas thereof and the trend of the body temperature of the user while he is staying within the area of interest.

Again, the possibility of acquiring the data recorded by the monitoring patch is limited to an operator—for example, a doctor or other healthcare professional—or the same user on whom the patch is applied who is considered to possess the necessary authorisation and/or credentials.

Preferably, the possibility of acquiring the data recorded by the monitoring patch is conditional on the user's body temperature exceeding the threshold value.

In one embodiment, the system further comprising a user device configured to:

activate a communication channel with the at least one monitoring patch, and transmit a unique code associated with a certificate in digital format of the user.

In addition, the at least one monitoring patch is configured to:

store in the memory module the unique code associated with the user's digital certificate, and transmit said unique code associated with the user's certificate in digital format to the detecting device and/or the reader device.

This makes it possible to check the possession of a certificate in digital format in an immediate and completely transparent way to the user without the need to associate the identification code of the monitoring patch to the certificate in digital format in advance. In addition, the system allows for the verification of certificates in digital format without the need for image capture tools such as cameras or video cameras, but using a radio frequency system, preferably a short-range one.

In one embodiment, the remote management entity is configured to:

generate a contact list comprising the patch identification codes included in the detector log of a selected detecting device comprising the patch identification code of a selected monitoring patch.

Preferably, the remote management entity is configured to:

include in the contact list a patch identification code included in the detector log of the selected detecting device, only if said patch identification code is associated with a timestamp comprised in a predetermined time interval. Even more preferably, said time interval is defined around the timestamp associated with the patch identification code of a selected monitoring patch.

This processing of the data stored by the remote management unit makes it possible to effectively identify which monitoring patches have been in close proximity to each other. Consequently, it is possible to identify which users have potentially come into contact with a selected user, in particular a user with a body temperature higher than the threshold value.

To this end, preferably, it is possible to associate each patch code with a corresponding user by accessing a restricted-access memory area of the remote management entity where confidential information is recorded such as a health record, an admission record, a personal record, a visitor record or by connecting to an appropriate restricted-access database or datacenter for the secure management of such data. Preferably, the ability to identify a user is conditional on the user's body temperature exceeding the threshold value.

In one embodiment, the at least one monitoring patch comprises an RFID or NFC device, preferably of a passive type. The memory module and the transceiver module are at least partially included in said RFID device or NFC device.

The Applicant has determined that the use of such technologies makes it possible to obtain a particularly compact, yet fully functional monitoring patch. In addition, the use of RFID or NFC technologies allows the integration into the system of widely used user devices, appropriately configured to operate in the system—for example, by running a corresponding software application.

In one embodiment, the at least one monitoring patch comprises at least one of:

a sensor configured to detect at least one of a biometric or vital parameter of the user, an accelerometer configured to measure an acceleration to which the monitoring patch is subjected, and a magnetometer configured to measure an orientation in space of the monitoring patch.

In such a case, the at least one detecting device is configured to store at least one of:

said at least one biometric or vital parameter of the user, a trend over time of said acceleration, and a trend over time of said orientation.

This additional data collected allows detailed information to be obtained on the identity, physical condition and/or movement of a user equipped with the monitoring patch.

In one embodiment, the at least one detecting device is configured to control a blocking element of the corresponding gate. For example, the detecting device is connected to the lock of a door or to the electric motor of a gateway which are arranged to selectively block transit through the gate.

In this case, as an addition or alternative to transmitting the alert message to a remote entity above, the detecting device is configured to switch or maintain the blocking element in a blocked state—such that transit through the gate is prevented—if the temperature measurement obtained from the patch is greater than said threshold value.

As a further addition or alternative to the foregoing, the at least one detecting device is configured to check for the presence of each received patch identification within a list of enabled patch identifications. If the received patch identification is comprised in the list, the detecting device is configured to switch or maintain the blocking element in a blocked state—such that transit through the gate is prevented. Otherwise, if the patch identification is not comprised in the list of enabled patch identifications, the detecting device is configured to switch or maintain the blocking element in an unblocked state—such that it allows transit through the corresponding gate.

In a dual embodiment, in the event that the patch identification received from a patch in proximity to the gate is comprised in the list, the detecting device is configured to switch or maintain the blocking element in an unblocked state—such that it allows transit through the corresponding gate.

Otherwise, if the patch identification is not comprised in the list of enabled patch identifications, the detecting device is configured to switch or maintain the blocking element in a blocked state—such that transit through the gate is prevented.

These solutions make it possible to restrict access to one or more sub-areas of the monitoring area based on a physiological condition of the user on whom the patch is applied and/or on his level of authorisation.

In one embodiment, the remote entity is configured to transmit to one or more detecting devices the identification code of each patch contained in an alert message, possibly via a blacklist—i.e., which has communicated a body temperature measurement that is higher than the threshold value.

Preferably, the detecting devices are configured to store the patch identification code reported by the remote entity and, therefore, to switch or maintain the blocking element in a blocked state—such that transit through the gate is prevented—if the presence of the patch associated with the reported patch identification code is detected in correspondence with the gate.

The distribution of the identification code to the detecting devices makes it possible to restrict the movements of a user within the monitored area, substantially limiting the possibility of interaction among subjects within the monitored area and the user who has a predetermined physiological condition—for example, an excessive body temperature.

In one embodiment, the at least one detecting device is configured to:
  determine a number of users equipped with a monitoring patch who entered a sub-area of said plurality of sub-areas through the at least one gate, and
  if the number of users determined is equal to a threshold value, switch or maintain the blocking element in the blocked state to prevent further users from entering said sub-area.

This solution allows the number of users within a sub-area of the monitored area to be limited in a simple and effective way. In other words, it is possible to automatically ensure that one or more monitored sub-areas are not overcrowded, limiting for example the spread of pathogens among users.

In one embodiment, the device is configured to alter or interrupt, preferably irreversibly, operation when removed from the epidermis of a user.

Preferably, at least a part of the transceiver module, of the memory module, of the sensor, and/or of the circuitry of the monitoring patch is configured to alter its operation in response to the removal of the monitoring patch from the epidermis of the user to be monitored. For example, the transceiver module comprises a portion configured to break when the monitoring patch is removed from the epidermis of the user to be monitored.

More preferably, the monitoring patch comprises support substrate having at least one pre-cut portion—so as to define a corresponding break line—which causes a division into at least two parts of the support during removal of the monitoring patch from the user's skin. Further, a portion of the transceiver module—e.g., the antenna—is made by means of a film of conductive material applied over said pre-cut portion of the support substrate, said portion of the transceiver module being configured to break during division into at least two parts of the support caused by removal of the patch.

In this way, an attempt to tamper with the device or swap identities can be prevented and, if necessary, unequivocally identified.

A different aspect of the present invention relates to a method for monitoring the conditions and movements of at least one user. The method comprises the steps of:
  applying at least one adhesive monitoring device for skin application or monitoring patch on the epidermis of the user to be monitored, said patch comprising an adhesive substrate for skin use in which are embedded or to which are bound at least:
    a sensor configured to detect a body temperature of the user,
    a memory module, configured to store data, and
    a transceiver module;
  by means of a detecting device arranged in correspondence with a gate, detect the presence of the at least one monitoring patch within a predetermined distance with respect to a gate associated with a sub-area of a plurality of sub-areas, the plurality of sub-areas defining a monitoring area;
  activating a communication channel between the at least one detecting device and the at least one monitoring patch to receive at least one temperature data detected by the user's body temperature sensor;
  transmitting a detector identification code associated with the at least one detecting device and a corresponding timestamp to the at least one monitoring patch detected within the predetermined distance, and
  storing in the memory module of the at least one monitoring patch each identification code of the detecting device and each corresponding timestamp received.

Preferably, the method also includes the steps of:
  by means of the at least one monitoring patch, transmitting a patch identification code, and
  by means of the detecting device, storing the patch identification code of the at least one monitoring patch, the user's body temperature measurement provided by the at least one monitoring patch and a timestamp associated with the reception of the patch identification code.

The above method allows to monitor the movements and one or more vital parameters of at least one user within an area of interest and/or sub-areas thereof, achieving the same advantages as described above in relation to the system in its embodiments.

Further features and advantages of the present invention will be more evident from the description of the accompanying drawings.

BRIEF DESCRIPTION OF THE DRAWINGS

The invention is described hereinbelow with reference to certain examples provided by way of non-limiting example and illustrated in the accompanying drawings. These drawings illustrate different aspects and embodiments of the present invention and reference numerals illustrating structures, components, materials and/or similar elements in different drawings are indicated by similar reference numerals, where appropriate.

FIG. 7 schematically illustrates a data log stored by the monitoring device of the system of FIG. 1;

FIG. 8 schematically illustrates a data log stored by a detecting device of the system of FIG. 1;

FIG. 10A is an example of temperature blacklists used in the monitoring procedure of FIG. 9;

FIG. 10B is an example of temperature blacklists used in the monitoring procedure of FIG. 9;

FIG. 11A is an example of authorisation blacklists used in the monitoring procedure of FIG. 9;

FIG. 11B is an example of authorisation blacklists used in the monitoring procedure of FIG. 9;

FIG. 17 is a flow chart of a procedure for the control of the certificate in digital format according to an embodiment of the present invention;

FIG. 18 is a flow chart of a procedure for associating the monitoring device with a certificate in digital form to a user thereof according to an alternative embodiment of the present invention, and FIG. 19 is a flow chart of a procedure for the control of the certificate in digital format according to an alternative embodiment of the present invention.

DETAILED DESCRIPTION OF THE EMBODIMENTS

Figure 1:
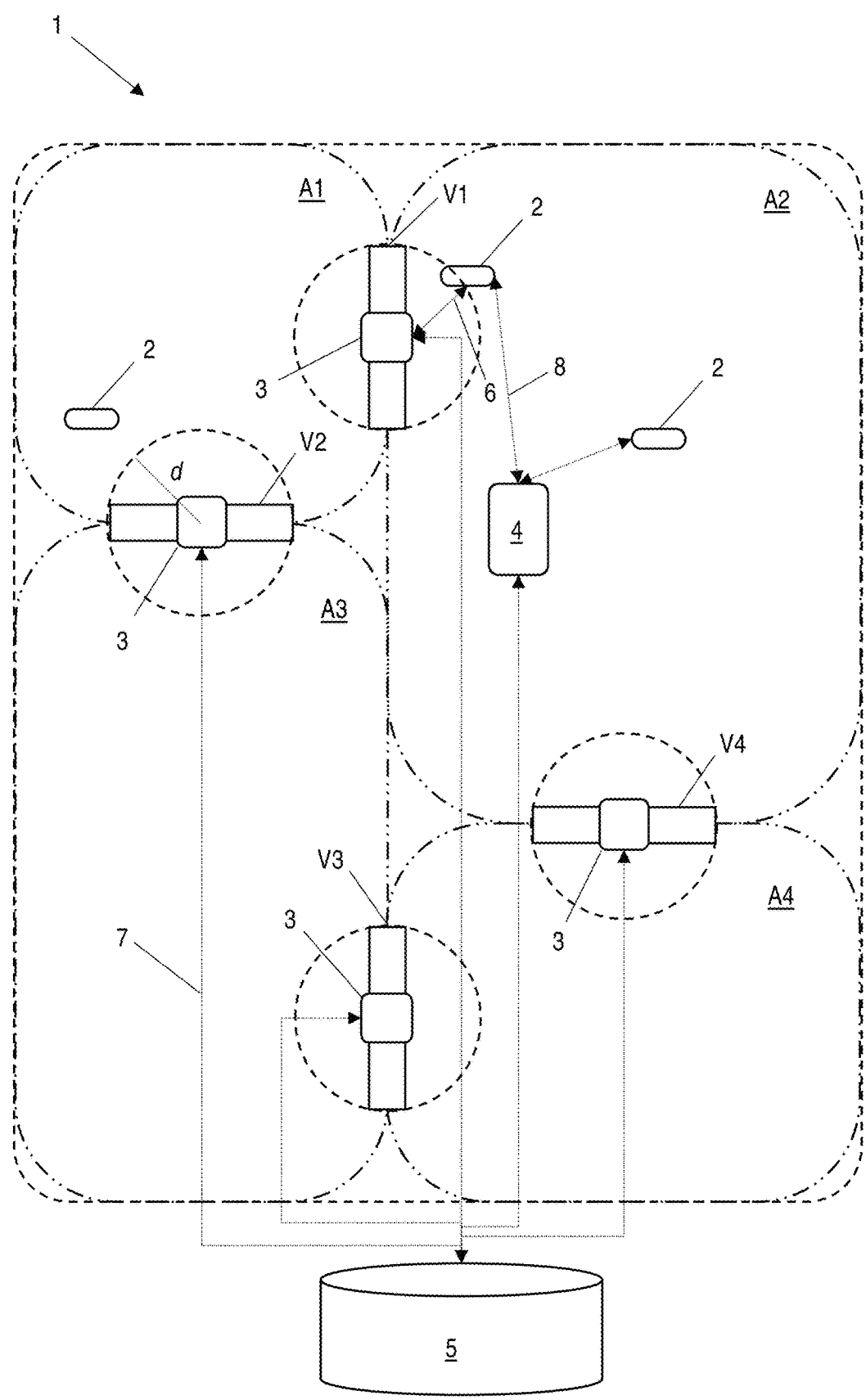
FIG. 1 schematically illustrates a monitoring system according to the present invention arranged within an area of interest.

While the invention is susceptible to various modifications and alternative constructions, certain preferred embodiments are shown in the drawings and are described hereinbelow in detail. It must in any case be understood that there is no intention to limit the invention to the specific embodiment illustrated, but, on the contrary, the invention intends covering all the modifications, alternative and equivalent constructions that fall within the scope of the invention as defined in the claims.

The use of "for example", "etc.", "or" indicates non-exclusive alternatives without limitation, unless otherwise indicated. The use of "includes" means "includes, but not limited to" unless otherwise indicated.

With reference to FIG. 1, numerical reference 1 means, as a whole, a monitoring system according to an embodiment of the present invention. The system 1 comprises one or more adhesive monitoring devices for skin application, preferably monitoring patches 2—hereinafter referred to simply as patches 2 for brevity's sake—, and a plurality of detecting devices,—hereafter referred to simply as detectors 3 for brevity's sake—, arranged within an area of interest A—for example, a building or a complex of buildings and appurtenant areas—and configured to detect the presence of the patches 2. Preferably, the system 1 also comprises a reader device 4—reader 4 for short in the following—configured to acquire data from the patches 2 and/or a remote processing unit, for example, a database 5 configured to acquire data from the detectors 3.

In particular, the area of interest A comprises in a non-limiting manner an open area—such as a park or an event area—or a building—such as a health care facility, a company, a shopping mall, a government building, a residential building, one or more selected portions of such buildings and/or of appurtenances of such buildings such as car parks, garages, parks, etc. In the example considered, the area of interest A is a portion of a building subdivided into different sub-areas A1-A4—for example, each corresponding to a room, a compartment or a group of compartments of a building, a corridor, a staircase, a car park, a garden, etc. In the preferred embodiment, the detectors 3 are arranged in proximity to a gate V1-V4—for example, a door, a gateway, a passage, an entrance, an exit, etc.—which allows to enter and/or exit the building from a corresponding sub-area A1-A4.

Figure 2:
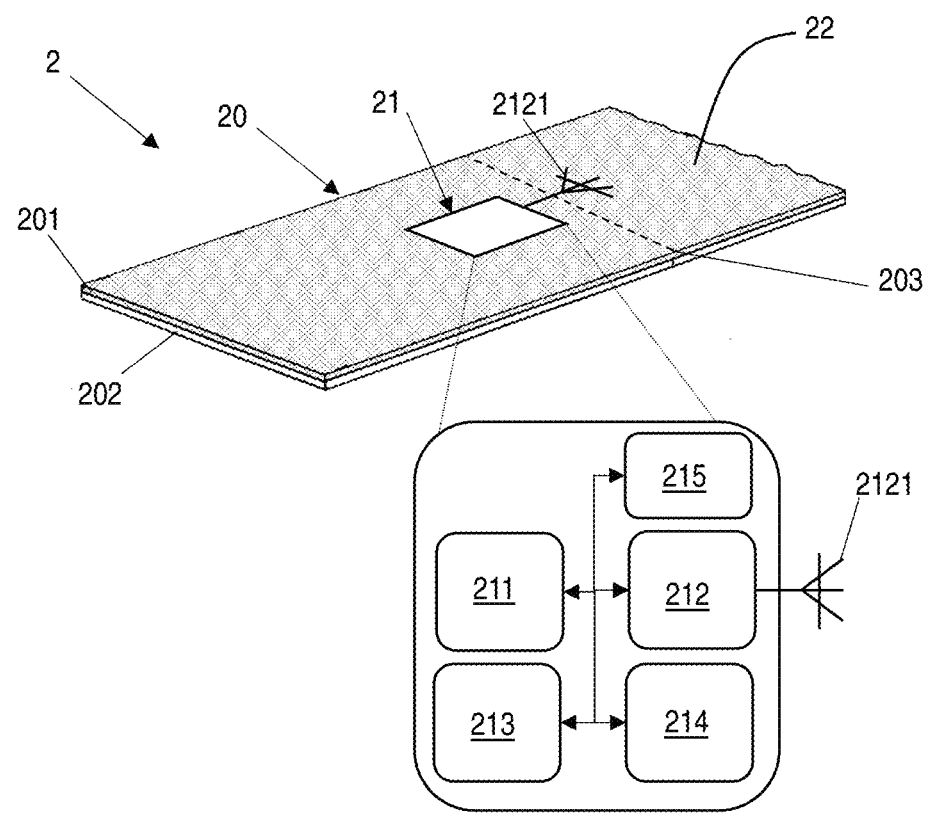
FIG. 2 schematically illustrates a monitoring device of the system of the Figure according to an embodiment of the present invention.

Turning now to FIG. 2, the generic patch 2, in accordance with an embodiment of the present invention, comprises a support substrate 20 and an electronic unit 21.

The support substrate 20 is conformed like a thin band, preferably microperforated to ensure breathability and even more preferably, pre-cut at predetermined positions to mark break lines (of which a break line 203 is schematically illustrated by a dashed line in FIG. 2) during removal or an attempt to remove from the skin, as explained in greater detail below. The support substrate 20 comprises a (first) main inner surface 201 configured to come into contact the body of a user to be monitored (not illustrated) during use, and a (second) main outer surface 202 configured to remain exposed to the external environment during use. Advantageously, the main inner surface 201 is covered with a layer of adhesive material 22, preferably biocompatible, suitable to ensure adhesion of the patch 2 to the user's epidermis—i.e., on the skin—also resisting washing and rubbing with clothes.

The electronic unit 21 comprises a memory module 211, a transceiver module 212 and a sensor module 213—in the preferred embodiment comprising at least one temperature sensor. Preferably, the electronic unit 21 also comprises a logic module 214. Possibly, a module capable of accumulating electrical energy 215 such as a battery or a capacitor.

The memory module 211 is configured to store data in non-volatile mode, preferably in binary format. Advantageously, the memory module 211 stores an identification code $ID_C$ of the patch 2, for example a string of binary digits. The transceiver module 212 is configured to transmit and receive electromagnetic signals, in particular radio frequency signals comprised in a predetermined frequency band. Preferably, the transceiver module 212 is also configured to absorb part of the energy of the received electromagnetic signals and use it to supply the electronic unit 21—according to a power generation technique better known by the terms energy scavenging or energy harvesting per se known and not described herein in detail for brevity's sake.

In a per se manner known, the transceiver module 212 also comprises an antenna 2121 for absorbing and transmitting said electromagnetic signals.

In a preferred embodiment, the antenna 2121 is made in such a way that it is significantly altered if the patch 2 is removed from the user's skin.

Preferably, the antenna 2121 is configured to become unusable when the patch 2 is removed from the user's skin. For example, a portion of the antenna 2121—such as a connecting element for the connection to the transceiver module—is configured to break or deform irreparably when the patch 2 is removed from a user's epidermis, thereby rendering the antenna 2121 useless.

In a non-limiting embodiment, the breaking effect of the antenna 2121 is achievable by making the antenna 2121 with a thin metal film printed on a corresponding portion of the support substrate 20 of the patch 2 configured to break during removal of the patch thereby also breaking the metal film.

For example, the support portion 20 is pre-cut so as to define the break line 203 on which a part of the antenna 2121 is printed. Thus, during removal of the patch 2 from the user's skin, the pre-cut portion gives way due to the tensile force exerted, causing a separation into two portions of the support substrate 20 along the break line 203. Accordingly, the metal film of the antenna 2121 breaks at the same time as the separation of said portions of the support substrate 20 of the patch 2.

The sensor module 213 is configured to detect at least one biometric parameter of the user. In the example considered, the sensor module 213 is configured to detect a body temperature of the user—possibly, the sensor module 213 may be conformed and arranged so as to at least partially come into contact with the user's skin. Finally, the logic module 214 is configured to control the operation of the other modules based on a set of instructions contained in the logic module itself and/or stored in the memory module 211.

Preferably, the electronic unit 20 or a part thereof—for example at least part of the memory module 211, of the transceiver module 212 and of the logic module 214—is configured to operate as a tag of the RFID or NFC technology.

Figure 3:
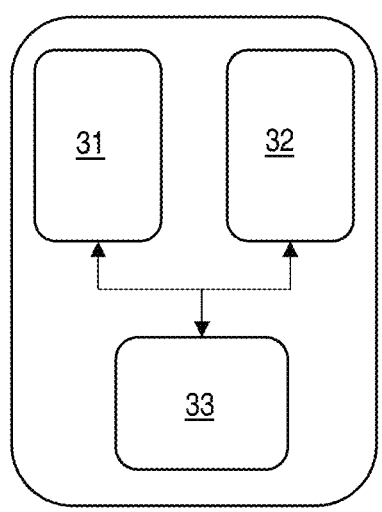
FIG. 3 is a block diagram of a detecting device of the system of FIG. 1 according to an embodiment of the present invention.
Figure 4:
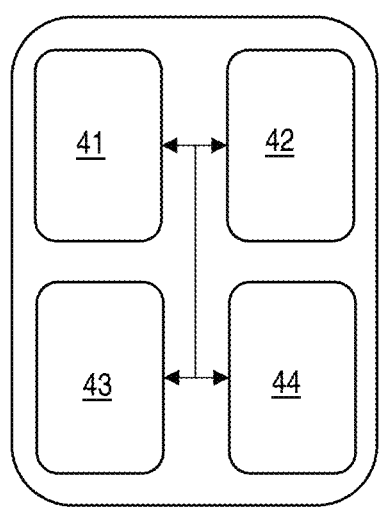
FIG. 4 is a block diagram of a reader device of the system of FIG. 1 according to an embodiment of the present invention.

Turning now to FIG. 3, the generic detector 3 comprises a transceiver module 31, a memory module 32 and, preferably, a control module 33. The transceiver module 31 is configured to transmit and receive electromagnetic signals, in particular radio frequency signals comprised in the frequency band used by the patch 2, in order to establish a communication channel 6 between the patch 2 and the detector 3 and to allow an exchange of data and energy between them. In addition, the transceiver module 31 is also configured to establish a communication channel 7—for example, by means of radio frequency signals or electromagnetic and/or optical signals via a wired line—with the database 5. The memory module 32 is configured to store data in non-volatile and/or volatile mode, preferably in binary format. Advantageously, the memory module 32 stores an identification code $ID_R$ of the detector 3, e.g. a string of binary digits that is unique to each detector 3. Finally, the control module 33 is configured to control the operation of the other modules based on a set of instructions contained in the logic module itself and/or stored in the memory module 32. Preferably, the control module 33 is configured to encrypt the data collected by the receiver 31 before storing them in the memory 32 or transferring them to the database 5.

In a preferred embodiment, the at least one detecting device is connected to a corresponding blocking element of the corresponding gate, such as a door or gateway, in order to control the operation thereof. For example, the detecting device is connected to a lock of a door or an electric motor of a gateway that blocks transit through the gate.

The reader 4 comprises a transceiver module 41, a memory module 42, a control module 43 and an interface module 44. In detail, the transceiver module 41 is configured to transmit and receive electromagnetic signals, in particular radio frequency signals comprised in the predetermined frequency band, so as to allow an exchange of data and energy between the reader 4 and the patch 2. Similarly to the foregoing, the memory module 42 is configured to store data in non-volatile and/or volatile mode, preferably in binary format, and the control module 43 is configured to control the operation of the other modules based on a set of instructions contained in the logic module itself and/or stored in the memory module 42. Finally, the interface module 44 is configured to present information and receive instructions from an operator of the reader.

Preferably, the control module 43 is configured to encrypt the data collected by the receiver 31 before storing it in the memory 32 and decrypt the encrypted data before making them available through the interface module 44.

In one embodiment, the reader 4 comprises an operator terminal (in a non-limiting manner: a computer, a tablet and/or a smartphone) of a healthcare professional, for example a doctor or the user himself. Preferably, the reader 4 implements a software application configured to encrypt the information provided by the patch 2 and retain it in the memory module 42 in a secure manner, limiting the possibility of access bound to the possession of specific credentials.

In one embodiment, the reader 4 is a device that is provided to authorised personnel—in particular, a doctor or the user—and the information is only accessible under predetermined conditions (e.g. if a body temperature higher than a threshold level is detected) and/or through specific access credentials, so as to ensure the confidentiality of the user information collected by the reader 4.

For example, the user can check his own body temperature as detected by the patch 2 in real time through his own reader device, such as a smartphone on which a dedicated patch reading software application is possibly installed and/or by means of a generic software application, such as a web browser.

Finally, as reported in FIG. 1, the database 5 is configured to exchange data with each detector 3 of the system 1 through the corresponding communication channel 7 and to store data received from the detectors 3 in a structured manner as described below. In addition, the database 5 is, preferably, configured to exchange data with the reader 4 through a communication channel 8 and/or a processing terminal (not illustrated, for example, a computer)—for example, by means of radio frequency signals or electromagnetic and/or optical signals via a wired line.

In one embodiment, the database 5 comprises or is linkable to an electronic health record—or similar repository of medical data—of the users of the system 1. In this case, the information acquired from the database 5 is associated with the corresponding health record of the user.

Preferably, such information is only accessible in case of pre-determined conditions and/or by means of specific access credentials, by authorised personnel—for example, a doctor or the user himself or herself—so as to guarantee the confidentiality of the user information.

Figure 5:
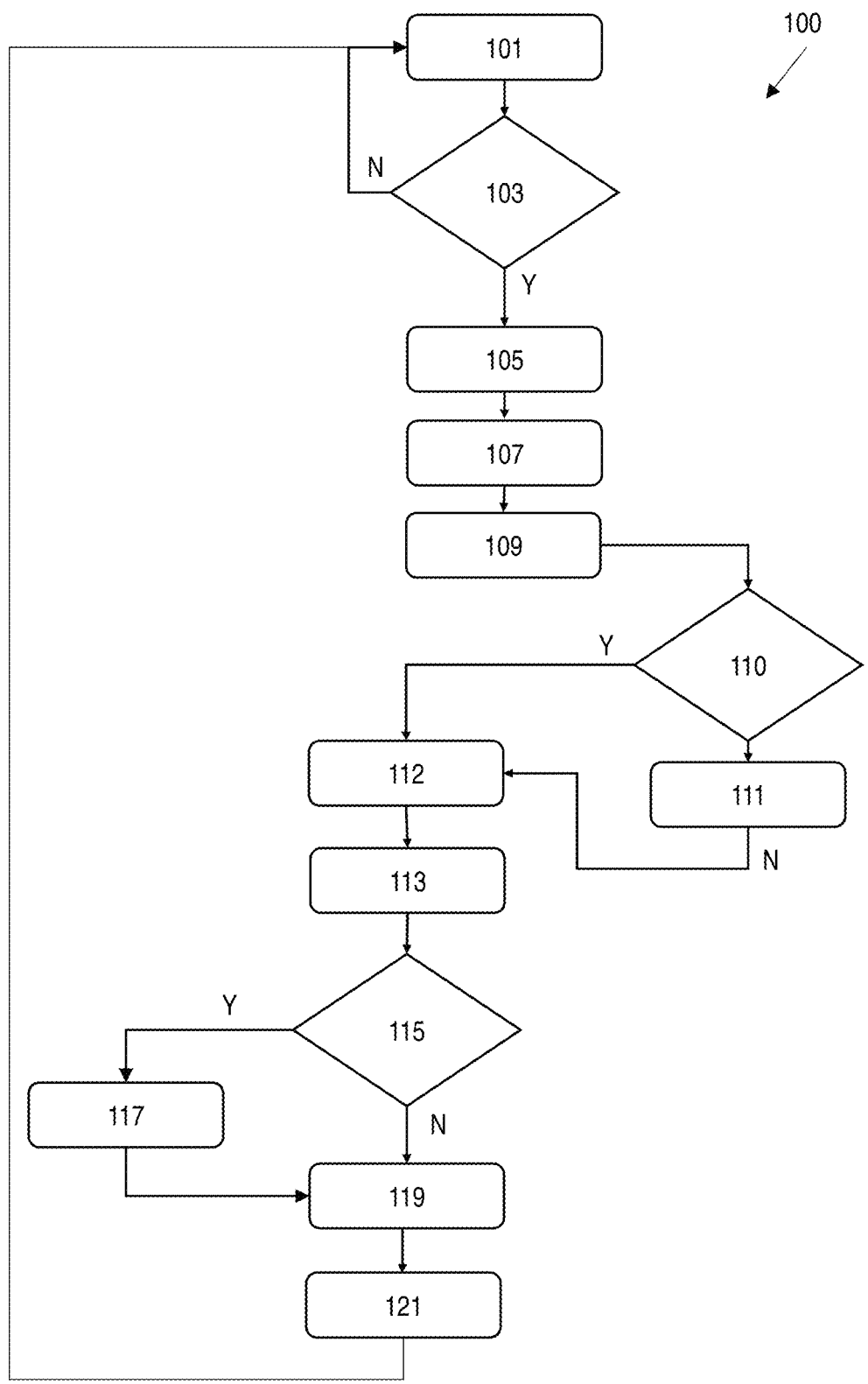
FIG. 5 is a flow chart of a procedure for monitoring a user implemented by the system of FIG. 1 according to an embodiment of the present invention.
Figure 6:
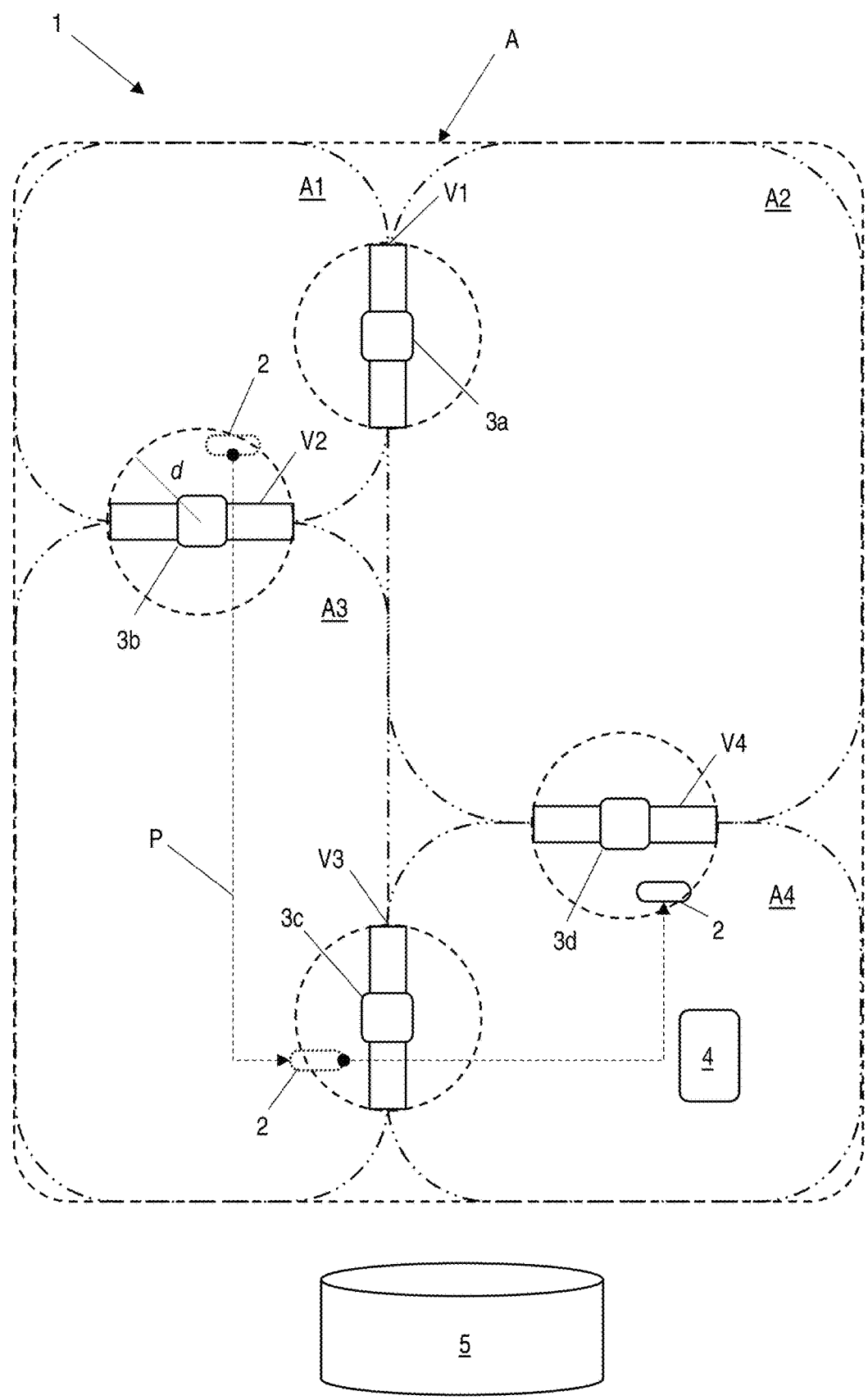
FIG. 6 schematically illustrates the path of a user carrying a monitoring device within the area of interest.

The system 1 allows monitoring, recording and checking the access, exit and/or crossing of one or more of the sub-areas A1-A4 within the area of interest A by a user equipped with a patch 2. For this purpose, in one embodiment of the present invention, the system 1 is configured to implement a monitoring procedure 100, of which FIG. 5 is a flow chart. The procedure 100 is described below considering FIG. 6 in which a generic patch 2 is illustrated which is applied to a user (not illustrated) moving along a path P in the area of interest A where four detectors 3a-3d are arranged, each in correspondence with a gate V1-V4 associated with a corresponding sub-area A1-A4.

Each of the detectors 3a-3d is configured to periodically output a search signal (block 101). In particular, the useful range of such a search signal defines a detection distance d within which a detector 3a-3d is able to successfully detect a patch 2. Preferably, the position and detection distance d of the detector 3a-3d are selected to ensure that the detector 3a-3d is able to detect any patch 2 crossing the corresponding gate V1-V4.

In a non-limiting embodiment, it is envisaged that the user performs a voluntary gesture such as stopping or reducing speed in proximity to the detector 3a-3d or, more generally, the gate V1-V4 to allow the data contained in the patch to be correctly recorded and the procedure 100 to be completed before proceeding to authorise the transit through the gate. For example, each detector 3a-3d comprises an interface element or an exposed portion in proximity to the corresponding gate V1-V4 to which the patch 2 is to be approached.

In an exemplary embodiment, the search signal comprises the identification code $ID_{Ra-d}$ of the corresponding detector 3a-3d outputting said search signal and, even more preferably, a timestamp or $t_S$ which contains an indication of an instant of time in which the search signal was transmitted.

As long as the user wearing the patch 2 does not come closer within the detection distance d one of the detectors 3a-3d arranged in the area of interest A (output branch N of the decision block 103) the electronic unit 21 of the patch 2 remains switched off. Conversely, when a path P of the user brings the patch 2 within the detection distance d of one of the detectors 3a-3d (output branch Y of decision block 103), the electronic unit 11 receives the search signal at the transceiver module 211 which uses the energy to supply the modules 211-215 (block 105). Once the modules 211-215 are activated, the electronic unit 21 of the patch 2 is configured to store, in the memory module 211, the identification code $IDR_{a-d}$ (block 107) and to store the corresponding timestamp $t_S$ (block 109) contained in the received search signal. In particular, each identification code $IDR_{a-d}$ is associated with the corresponding timestamp $t_S$ when stored in the memory module 211. Eventually, the patch 2 also stores a measurement $T_U$ of the user's body temperature measured by the sensor module 213 substantially at the reception of the search signal.

Preferably, the patch 2 is configured to store a list or log $R_C$ of patch 2 comprising each identification code $IDR_{a-d}$ associated with the detectors 3 to which the patch 2 has come closer within the detection distance d. Preferably, each identification code $IDR_{a-d}$ stored in the log $R_C$ is associated with the corresponding timestamp $t_{Sa-d}$ and, possibly, the corresponding measurement $T_U$ of the user's body temperature. As illustrated in FIG. 7, the log $R_C$ of the patch 2 that followed the path P illustrated in the example of FIG. 6 will contain three entries, each of which comprises an identification code $IDR_b$, $IDR_c$ and $IDR_d$ of the corresponding detector 3b, 3c, and 3d, the corresponding search signal of which is received. In addition, each entry of the log $R_C$ comprises the corresponding timestamps $t_{Sb}$, $t_{Se}$ and $t_{Sd}$, temperature measurement $TU_b$, $TU_c$ and $TU_d$. Advantageously, the entries of the log $R_C$ are sorted in chronological order based on the timestamp $t_{Sb}$, $t_{Sc}$ and $t_{Sd}$.

Optionally, if one or more of the write operations in the memory area 211 are unsuccessful (analysis performed at decision block 110)—for example, due to a depleted storage space in the memory 211 or due to a low level of energy given by an excessive distance of the patch 2 from a detector 3a-3d—(output branch N of the block 110) the patch 2 will communicate an appropriate error signal together with its patch identification IDc (block 111).

In the example considered, irrespective of the outcome of the write operations in the memory 211 (i.e., output branch Y of block 110 or downstream of block 111), it is contemplated that the patch 2 transmits a response signal whenever a search signal transmitted by one of the detectors 3a-3d (block 112) is received. The response signal transmitted by the patch 2 comprises a measurement $T_U$ of the user's body temperature measured by the sensor module 213 substantially at the generation of the response signal—prior to the transmission thereof—and, preferably, the patch identification code $ID_C$ of the patch 2 outputting the response signal.

Each detector 3a-3d, upon receiving the response signal transmitted by the patch, is, preferably, configured to store the identification code $ID_C$ of the patch 2 and the measurement $T_U$ of the user's body temperature in the memory module 32 (block 113). In addition, the detector also stores a timestamp $t_S$ indicative of an instant of response signal reception time; in particular, the timestamp $t_S$ is associated with the identification code $ID_C$ of the patch 2 and with the measurement Tu included in the response signal to which the timestamp $t_S$ refers.

Each detector 3a-3d is configured to analyse each of the measurement $T_U$ received from a patch 2, in the example considered, the measurement $T_U$ of the user's body temperature is compared to a threshold value—for example, a body temperature value starting from which the user is considered to be a user in a febrile state—(decision block 115).

In the event that the measurement $T_U$ is greater than the threshold value (output branch Y of block 115), the detector 3a-3d is configured to transmit an alert message to one or more remote entities, for example the database 5, the reader 4 and/or another management or control device (such as an operator terminal of one or more operators within the area of interest and/or a server, not illustrated in the figures) (block 117).

Advantageously, the alert message may comprise—in a non-limiting manner—one or more of the following information:
- the indication that a user in a febrile state has passed through the gate;
- the measurement $T_U$ of the user's body temperature that has exceeded the threshold value;
- the patch identification code $ID_C$ of the patch 2 worn by that user in a febrile state;
- the timestamp $t_{Sa}$, $t_{Sb}$ and $t_{Sd}$ associated with the measurement Tu.

Once the alert message has been transmitted or if the measurement $T_U$ is lower than the threshold value (output branch N block 115), each detector 3a-3d is preferably configured to transmit to the database 5 a detection message, for each response signal received by the detector 3a-3d (block 119). In this example, the detection message comprises the identification code $ID_C$ of the patch 2, the measurement $T_U$ and the corresponding timestamp $t_S$.

The database 5 is configured to store the data contained in each detection message received (block 121). In one embodiment, the database 5 is configured to generate a database list or log $R_{DBa-d}$ for each detector 3a-3d included in the system 1. Each log $R_{DBa-d}$ lists the identification codes IDc of each patch 2 detected by the same detector 3a-3d. In more detail, each log $R_{DBa-d}$ comprises an entry for each identification code $ID_C$, which comprises, in addition to the identification code $ID_C$ under consideration, the corresponding measurement $T_U$ of the user's body temperature and the corresponding timestamp $t_S$, as illustrated schematically in FIG. 8.

The procedure 100 just described is substantially repeated without interruption by the elements of the system 1, as long as the system 1 is operational.

In an alternative embodiment, the system 1 is configured to selectively allow transit through a gate among the sub-areas of the monitored area to a user equipped with a corresponding patch only if one or more predetermined conditions are met. In this embodiment, each detector 3a-3d is connected to a blocking element—a door, gateway, turnstile, etc. (not illustrated for simplicity's sake)—of the corresponding gate V1-V4 and configured to control the operation thereof. For example, each 3a-3d detector is connected to a lock of a door, a turnstile control module or to the electric motor of a gateway (not illustrated for simplicity's sake) configured to selectively block transit through the corresponding gate V1-V4.

Figure 9:
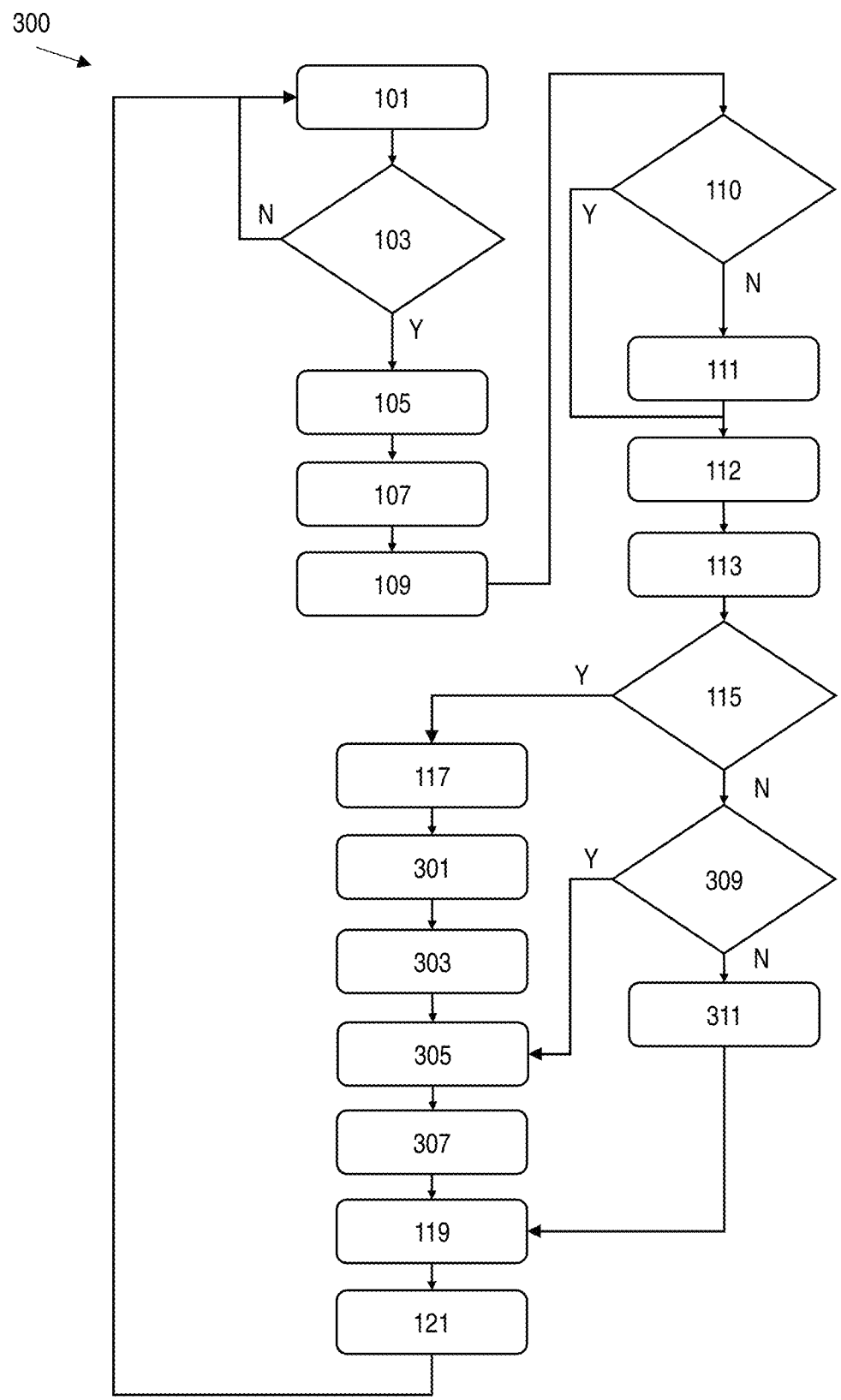
FIG. 9 is a flow chart of a procedure for monitoring the movements of a user implemented by the system of FIG. 1 according to a further embodiment of the present invention.

In this embodiment, the system 1 is configured to implement a transit monitoring and restriction procedure 300, of which FIG. 9 is a flow chart. In particular, the procedure 300 differs from the procedure 100 described above in that it follows where the corresponding steps are marked by the same numerical references and their description is not repeated for brevity's sake.

According to the procedure 300, upon receipt of the alert message (at block 117) regarding a temperature measurement $T_u$ greater than the threshold value, the database 5 is configured to enter the patch identification code $ID_C$ included in the alert message into a temperature blacklist (block 301), which is transmitted to each detector 3a-3d of the system periodically or each time a new entry is made therein (303).

In addition, the detector 3a-3d that has identified the temperature measurement $T_U$ greater than the threshold value switches or maintains in a blocked state the blocking element of the gate V1-V4 so as to prevent the user wearing the patch 2 from crossing the gate (block 305). Optionally, the detector 3a-3d that has identified the temperature measurement $T_U$ greater than the threshold value is switched to output a local alert to signal the presence of a user in a febrile state (block 307).

Thereafter, the operation continues as described in procedure 100 in relation to block 119.

Otherwise, when a temperature measurement $T_U$ greater than the threshold value is not identified (output branch N of block 115), the detector 3a-3d is configured to check whether the patch identification IDc transmitted by a patch 2—as described in relation to block 112—is included in an unauthorised blacklist or in the temperature blacklist described above (decision block 309). The unauthorised blacklist is a list of patch identifications IDc associated with users who are not authorised to access a particular sub-area A1-A4 of the monitored area or, in other words, who are not allowed to pass through one or more of the gates V1-V4, possibly in a specific direction (e.g. from sub-area A1 to sub-area A2 through gate V1 with reference to the diagram in FIG. 1). The authorisation blacklist is preferably stored in the database 5 and provided or analysed by each detector 3a-3d of the system 1 in a manner similar to that described above in relation to the temperature blacklist mutatis mutandis.

In case the patch identification is included in at least one blacklist (output branch Y of block 309), the procedure 300 provides for blocking transit through the gate V1-V4 associated with the detector 3a-3d that received the patch identification IDc under consideration—switching to block 305 described above.

Otherwise, if the patch identification is not included in a blacklist (output branch N of block 309), the detector 3a-3d switches or maintains in an unblocked state the blocking element of the corresponding gate V1-V4 so as to allow the user wearing the patch 2 to cross the gate (block 311).

Thereafter, the operation continues as described in procedure 100 in relation to block 119.

As illustrated in FIGS. 10A and 10B, the temperature blacklist $BL_T$ comprises a list of identification codes IDc (FIG. 10A) or, more preferably, the temperature blacklist $BL_T'$ comprises a column comprising the identification codes IDc and a column comprising the relevant measured temperatures (FIG. 10B). Similarly, the authorisation blacklist $BL_A$ comprises a list of identification IDc (FIG. 11A) or, more preferably, the authorisation blacklist $BL_A'$ comprises a column comprising the identification codes IDc and at least one column in which the sub-areas A1-A4 to which access is not allowed are indicated (FIG. 11B).

Figure 12:
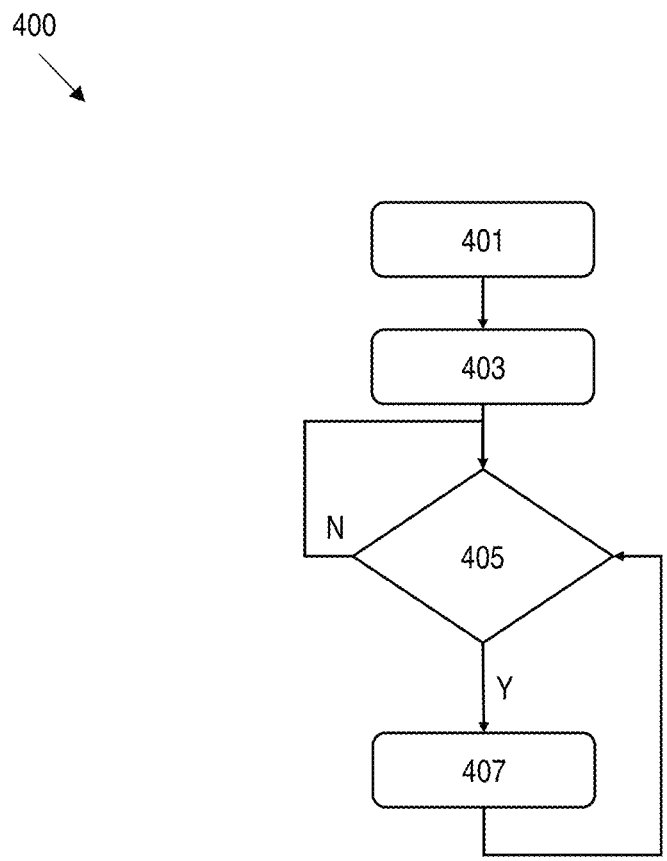
FIG. 12 is a flow chart of a procedure for limiting the number of users in the monitored sub-areas of the system of FIG. 1.

Additionally or alternatively, the system 1 is configured to perform a procedure 400 for restricting the number of users within an area, illustrated schematically in FIG. 12.

In detail, each detector 3a-3d is configured to detect the direction of crossing of the respective gate V1-V4 by each user equipped with patch 2 (block 401). For example, the detectors are configured to measure a flight time of multiple consecutive signal transmissions between each patch 2 and the detector 3a-3d as long as the patch 2 is within the detection distance d of the detector 3a-3d.

Based on the crossings of each gate V1-V4 and on the direction of these crossings determined by the detectors 3a-3d, a number of users present in the sub-areas A1-A4 is calculated (block 403).

For example, the database 5 contains a counter for each of the sub-areas A1-A4. A generic counter is incremented when one of the detectors 3a-3d signals the movement of a user equipped with patch 2 through the respective gate V1-V4 towards the corresponding sub-area A1-A4.

Conversely, the generic counter is incremented when one of the detectors 3a-3d signals the movement of a user equipped with patch 2 through the respective gate V1-V4 outside the corresponding sub-area A1-A4.

The procedure 400 includes verification that the number of users in the sub-areas A1-A4 is lower than a respective threshold value (decision block 405). For example, detectors 3a-3d are configured to periodically check that the counters stored in the database 5 comprise a value lower than a respective threshold value.

If the number of users present in the sub-areas A1-A4 is lower than a respective threshold value (output branch Y of block 405), no action is taken. Conversely, if the number of users present in the sub-areas A1-A4 reaches the threshold value (output branch N of block 405), the procedure 400 provides for preventing access to the sub-area A1-A4 in which the number of users equals the threshold value until the number of users in the sub-area A1-A4 falls below the threshold value (block 407). For example, the detectors 3a-3d arranged in correspondence with the gates V1-V4 allowing access to the sub-area A1-A4, in which the limit number of users is reached, switch or maintain in a blocked state the blocking element of the gate V1-V4 so as to prevent further users equipped with a patch 2 from crossing the gate towards the sub-area A1-A4 under consideration. Conversely, the detectors 3a-3d are configured to allow the users equipped with a patch 2 to exit by switching the blocking element of the gate V1-V4 into an unblocked state, when a user within the sub-area A1-A4 under consideration approaches the gate V1-V4. In this way, it is possible to ensure that in each sub-area A1-A4 the number of users does not exceed a maximum number.

Figures 13, 14:
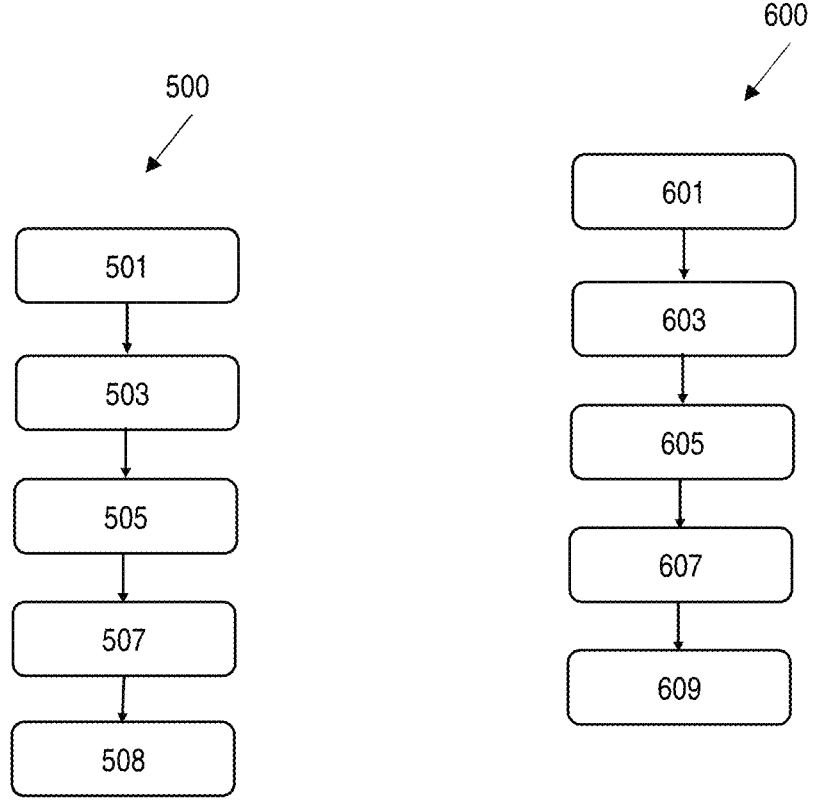
FIG. 13 is a flow chart of a procedure for reading the data stored in the monitoring device of the system of FIG. 1.
FIG. 14 is a flow chart of a procedure for analysing data stored in a database of the system in FIG. 1.

In one embodiment, it is envisaged that a procedure 500 for reading a patch 2 can be implemented, illustrated schematically by the flow chart in FIG. 13. The procedure 500 involves using the reader 4 in order to acquire data stored in the patch 2, in particular the log $R_C$ of the patch 2.

In detail, the patch 2 is brought within a reading distance dl from the reader 4 (block 501), for example within a range of a reading signal transmitted by the reader 4. When the read signal is received, the patch 2 is configured to transmit a corresponding response signal (block 503). In particular, the response signal transmitted by the patch 2 comprises the log $R_C$. The reader 4 is configured to store the log $R_C$ in its memory module 42 (block 505). Finally, the reader 4 is configured to present the information contained in the log $R_C$ in an intelligible format to an operator (not illustrated) by means of the interface module 44 (block 507). Optionally, the reader 4 is configured to connect to a remote entity, for example the database 5, and provide the log $R_C$ for long-term storage in the database 5 and/or to allow the information contained in the log $R_C$ to be processed (block 508).

In addition or alternatively, in one embodiment, the possibility of implementing a procedure 600 for analysing the data stored in the database 5, schematically illustrated by the flow chart of FIG. 14, is provided.

The procedure 600 is started on request, by an external entity—for example, by the reader 4 or a user terminal of an operator sending a data request message—(block 601). Alternatively, the procedure 600 is started automatically, upon reception of an alert message by one of the detectors 3a-3d.

Subsequently, the selection of a patch identification code $ID_C$ (block 603), the selection of one or more patch identification codes of detector $ID_{Ra-d}$ (block 605) and, preferably, the selection of one or more time intervals $\Delta t$ is provided (block 607). For example, the patch identification code $ID_C$, at least one detector identification code $ID_{Ra}$—and the at least one time interval $\Delta t$ selected are included in the data request message transmitted by the reader 4 (or other user terminal).

Alternatively, the selection of the patch identification code $ID_C$, of the at least one detector identification code $ID_{Ra-d}$ and of the at least one time interval $\Delta t$ may be performed after a communication channel is established between the reader 4 and the database 5. In case the procedure 300 is started by an alert message, the patch identification code $ID_C$ contained in the alert message itself corresponds to the patch identification code $ID_C$, the at least one detector identification code $ID_{Ra-d}$ corresponds to the detector identification code that outputted the alert message and, preferably, the time interval $\Delta t$ is determined based on the corresponding timestamp $t_S$—for example, the time interval $\Delta t$ is defined as around the timestamp $t_S$.

The database 5 is then configured to create a list $L_{a-d}$ (non illustrated) comprising all patch identification codes IDc included in a respective log $R_{DBa-d}$ selected and associated with a timestamp $t_S$ included in the time interval $\Delta t$ (block 609). The list $L_{a-d}$ associated with each detector identification code $ID_{Ra-d}$ is finally transmitted to the external entity through a response message.

However, it is clear that the examples reported above must not be interpreted in a limiting sense and the invention thus conceived is susceptible of numerous modifications and variations.

For example, the logic module of the electronic unit of the patch may be integrated at least partially into one or both of the transceiver and memory modules.

In an alternative embodiment (not illustrated), the electronic unit may comprise only a battery or similar electrical energy storage device, rather than comprising an energy harvesting apparatus.

In alternative embodiments, the electronic unit of the patch may comprise one or more sensors that are additional, or alternative to the temperature sensor. Such sensors are configured to detect a vital or biometric parameter of the user—for example, a heartbeat, a skin pH, skin surface electrical conductivity, etc. Alternatively or in addition, the patch may be equipped with one or more between accelerometers and/or magnetometers so as to allow an accurate analysis of the movement and/or the speed of the user within the monitored area.

In another embodiment (not illustrated), the transceiver module may comprise a reactive element—for example, a capacitor or inductor—configured to mechanically deform by modifying its own impedance, and hence a transceiver frequency, when the device is removed from the user's epidermis.

In an alternative embodiment, nothing prevents a part of the memory, of the sensor and/or of a further circuitry—e.g., circuitry of connection among the other electronic elements—of the monitoring patch from being configured to alter its operation in addition to or as an alternative to the transceiver module in response to the removal of the monitoring patch from the epidermis of the user to be monitored.

Additionally or alternatively, altering the device activates a secondary circuit configured to transmit a corresponding tampering message when the patch is removed from the user's epidermis.

Moreover, nothing prevents the patch from being equipped with a medicine designed to release a chemical substance through the epidermis or to protect a wound in addition to the electronic unit.

In one embodiment (not illustrated), it is contemplated that the patch is configured to absorb energy from a first search signal and to record the detector identification code and the relative timestamp and/or transmit its own patch identification code and the body temperature measurement, upon receipt of a second search signal.

In one embodiment (not illustrated), the search signal does not comprise the detector identification code and the timestamp, which are sent by means of a special message from the detector to the patch after the latter has transmitted a signal in response to the search signal.

In an alternative embodiment (not illustrated), the monitoring device comprises a wristband or a band equipped with an electronic unit similar to that described above.

In an alternative embodiment (not illustrated), the detectors are configured to download, preferably periodically, one or more blacklists or enabled lists from the database. Alternatively, the detectors are configured to transmit each identification code to the database the first time it is detected within the detector range and then receive an authorisation message confirming whether or not the user can pass through the gate associated with the detector. The detector will block or allow transit through the gate according to the content of the authorisation message.

In one embodiment, one or more detectors are configured to detect whether the patch and thus the user is approaching the gate or not. For example, each detector is configured to determine the approach of a patch by identifying a change in the flight time, a change in power between two or more messages exchanged with the patch in a sequence of successive time instants and/or through movement information provided by the patch itself if equipped with accelerometers and/or magnetometers.

In one embodiment (not illustrated), the detection message transmitted by the detectors may comprise more than one triad of the data associated with a single detected patch. For example, each detector is configured to transmit a detection message periodically—e.g. once every hour, every 4-8, daily. In this case, the detection message comprises a triad of data—that is, the patch identification code, the body temperature measurement and the corresponding timestamp—associated with each patch detected between transmissions. Alternatively, each detector is configured to transmit a detection message after receiving a predetermined identification code number.

In one embodiment, the system is implemented in a hospital facility where inpatients, staff and/or visitors to the hospital facility are equipped with a patch, so that the temperature and/or other biometric parameters and the movements of each individual within the facility are automatically tracked. This makes it possible to accurately reconstruct the movements within the facility of an individual potentially suffering from an infectious disease and all possible contacts with other people within the facility. This allows to prevent, or at least substantially limit, the spread of infectious diseases within the facility. In addition, the system allows the localisation and/or limitation of the possibility of movements within the facility, substantially in real time, of an individual whose body temperature and/or other vital parameters do not fall within an interval of acceptable values.

In one embodiment in a remote entity, e.g. the database, the information of all the $ID_C$'s worn by and belonged to each user of the system over time is recorded in order to be able to uniquely associate the detections made at the gates with the respective user and track their presence, transits and biometric and vital parameters, even when the patch is replaced due to wear and/or malfunction reasons.

In an alternative embodiment (not illustrated), the detectors are configured to communicate with each other a number of crossings of the respective gate to determine the number of users within the sub-areas without the need to communicate with the database.

As will be apparent to the person skilled in the art, one or more steps of the procedures 100, 300, 400, 500 and 600 and possible variants thereof described above may be performed in parallel with each other or in an order different from that presented above. Similarly, one or more optional steps may be added or removed from one or more of the above described procedures.

In particular, in alternative embodiments (not illustrated) the procedure for creating and controlling the temperature blacklist can be implemented independently of the control of enabling blacklists and vice versa.

Further, in addition or alternatively to maintaining one or more blacklists and checking for the presence of patch identifications therein, in alternative embodiments (not illustrated), the system is configured to maintain one or more whitelists and check for the presence of patch identifications therein.

Figure 15:
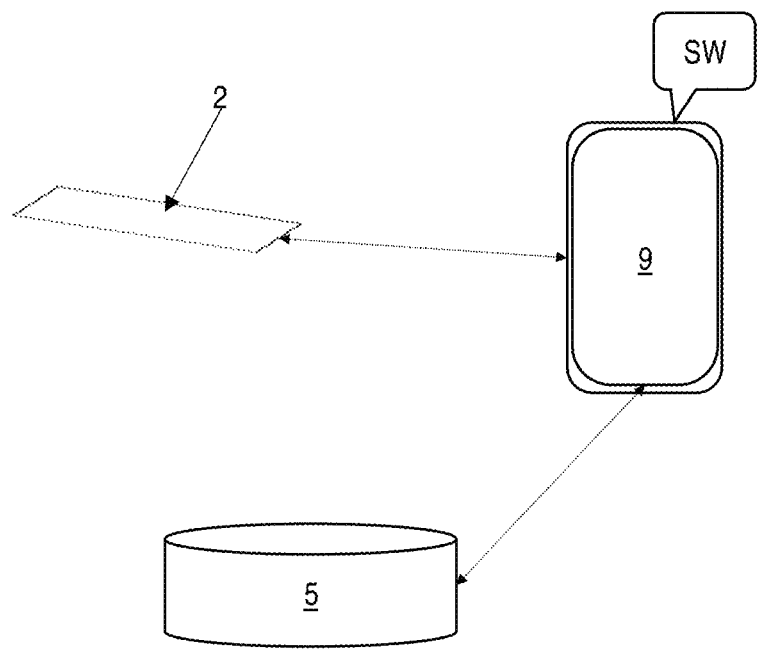
FIG. 15 schematically illustrates a user electronic device interacting with the monitoring device included in the system according to an alternative embodiment of the present invention.

In an alternative embodiment, the system 1 comprises an electronic user device, user device 9 (as illustrated schematically in FIG. 15) in short for example a smartphone, through which the patch can be associated with a certificate in digital format associated with the user, for example a vaccination or prophylaxis certificate such as the so-called EU Digital COVID Certificate.

Figure 16:
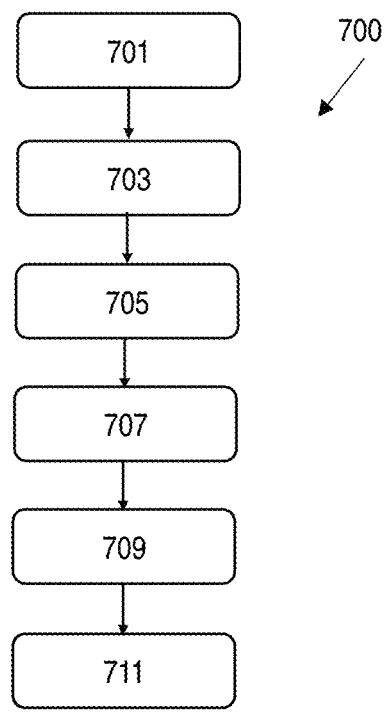
FIG. 16 is a flow chart of a procedure for associating the monitoring device with a certificate in digital format to a user thereof according to an embodiment of the present invention.

In particular, the system 1 is configured to implement a procedure 700 for associating the patch 2 applied to the user's skin with a certificate in digital format of the user himself—of which FIG. 16 is a flow chart. For this purpose, the user device 9 comprises the hardware necessary to establish a data communication channel with the patch 2 and executes a software application SW configured to manage a data exchange between the user device 9 and the patch 2—for example, via an NFC communication—and between the user device and the database 5 and/or a different remote processing entity (not illustrated), such as a distributed service for verifying certificates in digital format—for example, via a WiFi or mobile data network.

After the patch 2 has been applied to the user's skin, the user device 9 is configured—via the software application SW—to establish a communication channel with the patch 2 in order to receive the identification code $ID_C$ thereof. In particular, the user device transmits a user search signal (block 701) which is received by the transceiver module 211, which uses its energy to supply the modules 211-215 (block 703). Once the modules 211-215 are activated, the electronic unit 21 of the patch 2 is configured to transmit the patch identification code $ID_C$ (block 705).

The patch code $ID_C$ is received by the user device 9 (block 707), from which it is associated with the certificate in digital format, by sending an association request—containing the patch code $ID_C$—to the database 5 or to a distributed service for verifying certificates in digital format (block 709) that associates the patch code $ID_C$ with the user's certificate in digital format (block 711).

In an alternative embodiment (not illustrated), the user device 9 after receiving the patch identification code, is configured to establish a communication channel with a remote entity, and transmit the patch identification code. In this case, it is the database 5 or the distributed service for verifying certificates in digital format that associates the patch identification code with the file representative of the user's certificate.

In this case, the system 1 is preferably configured to perform a digital format certificate control procedure 800 in parallel or in series with one of the procedures 100, 300 and/or 400.

In detail, when one of the detectors 3a-3d receives the patch identification IDc contained in the response signal—as described in relation to block 112 —, the detector is configured to send a verification request to the database 5 or to the distributed service for verifying certificates in digital format (block 801). The verification request contains the identification code $ID_C$.

The database 5, or the distributed service for verifying certificates in digital format, checks for the presence of a valid certificate in digital format associated with the identification code $ID_C$ (decision block 803). If a valid certificate in digital format associated with the identification code $ID_C$ (output branch Y from block 803) is identified, the database 5, or the distributed service for verifying certificates in digital format, sends a positive response (block 805) according to which, preferably, the detector 3a-3d records a positive verification together with the identified code $ID_C$, the temperature measurement $T_U$ and the timestamp $t_S$ (block 807). Otherwise, if a valid certificate in digital format associated with the identification code $ID_C$ (output branch N from block 803) is not identified, the database 5, or the distributed service for verifying certificates in digital format, sends a negative response (block 809) based on which the detector 3a-3d records a negative verification together with the identified code $ID_C$, the temperature measurement $T_U$ and the timestamp $t_S$ (block 811) and generates an alert message (block 813) in a manner similar to what is described in relation to block 117 and, preferably, it switches or maintains in a blocked state the corresponding blocking element of the gate V1-V4 so as to prevent the user wearing the patch 2 from crossing the gate (block 815), in a manner similar to what is described in relation to block 305.

In an alternative embodiment, an alternative procedure 900 of association of the patch 2 is performed, according to which the user device transmits a user search signal comprising a unique code—or file—representative of the certificate in digital format—for example a hash code or an xml file containing all or part of the data included in the certificate in digital format, preferably encrypted—(block 901) which is received by the transceiver module 211 which uses the energy to supply the modules 211-215 (block 903). Once the modules 211-215 are activated, the electronic unit 21 of the patch 2 is configured to store the unique code or a file—representative of the certificate in digital format in the memory 211 (block 905).

In this alternative embodiment, a digital format certificate control procedure 1000 is implemented, which differs from the procedure 800 in that it provides that the response signal transmitted by the monitoring patch 2 comprises the unique code—or the file—representative of the certificate in digital format in addition to the patch identification $ID_C$—described in relation to block 112. Consequently, the detector is configured to send a verification request to the database 5 or to the distributed service for verifying certificates in digital format (block 1001). In this case, the verification request contains the unique code of the certificate in digital format instead of the patch identification IDc. Furthermore, the procedure 1000 comprises a sequence of steps (blocks 1003-1015) corresponding to the remaining steps of procedure 800 described in relation to blocks 803-815, mutatis mutandis.

Similarly, a single, or a combination of two or more, of the procedures 100, 300, 400, 500, 600, 700 800, 900 and 1000 and possible variants thereof presented above, form a method for monitoring users within an area of interest. In addition, one or more steps of the same procedure or of different procedures may be performed in parallel between each other or with an order different from the above described one. Similarly, one or more optional steps can be added or removed from one or more of the procedures described above.

For example, nothing prohibits implementing a method (not illustrated) combining the methods 700 and 900, in which the user device first performs an attempt to store the unique code—or the file—representative of the certificate in digital format in the patch (in a manner similar to that described in method 900) and, in case the storage fails—for example, in case of an insufficient memory space on the patch—the user device associates the patch identification code with the unique code—or with the file—representative of the certificate in digital format and transmits such data to the database, or to the distributed service for verifying certificates in digital format. Alternatively, the user device sends only the patch identification code to the database, or to the distributed service for verifying certificates in digital format that performs the association with the unique code— or to the file—that is representative of the certificate in digital format.

Again, in an alternative embodiment (not illustrated), the methods 700 and 900 are performed in parallel so as to associate the patch identification code to the unique code— or to the file— representative of the certificate in digital format both on the patch and on the database, or to the distributed service for verifying certificates in digital format so as to allow cross-checking.

Naturally, all the details can be replaced with other technically-equivalent elements.

In conclusion, the materials used, as well as the contingent shapes and dimensions of the aforementioned devices, apparatuses and terminals, may be any according to the specific implementation requirements without thereby abandoning the scope of protection of the following claims.

The invention claimed is:

1. A system for monitoring condition and movements of at least one user, comprising:
    at least one adhesive monitoring device for skin application or at least one monitoring patch, applicable to the epidermis of a user to be monitored, the at least one monitoring patch comprising an adhesive substrate for skin use in which are embedded or to which are bound at least:
        a sensor configured to detect at least one body temperature of the user,
        a memory module configured to store data, and
        a transceiver module configured to absorb supplied electrical energy from an electromagnetic radiation received by an antenna, and
    a plurality of detecting devices each detecting device being located in correspondence with at least an access gate to a sub-area of a plurality of sub-areas, the plurality of sub-areas defining a monitoring area,
wherein each detecting device is configured to:
detect presence of the at least one monitoring patch within a predetermined distance from the corresponding gate;
activate a communication channel with the at least one detected monitoring patch, and
wherein the at least one monitoring patch is configured to:
transmit a user's body temperature data,
wherein
each detecting device is configured to:
transmit to the at least one detected monitoring patch an identification code of the at least one detecting device and a corresponding timestamp, and
the at least one monitoring patch is configured to:
store in the memory module the identification code and the corresponding timestamp received from each detecting device with which the communication channel has been established.

2. The system according to claim 1, wherein the at least one monitoring patch is further configured to transmit a patch identification code, and
wherein the detecting device that detects the at least one monitoring patch is configured to:
store the patch identification code of the at least one monitoring patch, the data of user's body temperature provided by the at least one monitoring patch and a timestamp associated with the reception of the patch identification code; and
detect whether the body temperature data is indicative of a body temperature higher than a threshold value, and in case the body temperature measurement is greater than said threshold value:
establish a communication channel with a remote entity,
transmit an alert message, said alert message comprising the patch identification code of the monitoring patch that transmitted the body temperature data, and the corresponding timestamp.

3. The system according to claim 2, wherein the monitoring patch is configured to:
transmit each identification code and corresponding timestamp received from each detecting device stored in the memory module, and
wherein the detecting device that detects the at least one monitoring patch is configured to:
include in said alert message each identification code and the corresponding timestamp received from each detecting device stored in the memory module.

4. The system according to claim 1, further comprising a user device configured to:
activate a communication channel with the at least one monitoring patch to receive a patch identification code transmitted by the at least one monitoring patch, and
associate said patch identification code with a unique code or a file representative of certificate of the user certified in digital format, and
establish a communication channel with a remote entity, and
transmit the patch identification code and the unique code or a file representative of certified certificate of the user in digital format associated, or
establish a communication channel with a remote entity, and
transmit the patch identification code, and
wherein said remote entity is configured to:
associate said patch identification code with a unique code or a file representative of the user's certificate.

5. The system according to claim 1, further comprising a reader device configured to:
activate a communication channel with at least one monitoring patch, and
wherein the monitoring patch is configured to:
transmit each identification code and the corresponding timestamp received from each detecting device stored in the memory module.

6. The system according to claim 1, further comprising a user device configured to:
activate a communication channel with the at least one monitoring patch, and
transmit a unique code or a file representative of certificate in digital format of the user, and
wherein the at least one monitoring patch is configured to:
store in the memory module the unique code or the file representative of the user's certificate in digital format, and
transmit said unique code or the file representative of the certificate of the user certified in digital format to the detecting device and/or to the reader device.

7. The system according to claim 2, further comprising a remote management unit and a plurality of monitoring patches, each monitoring patch being applied to a respective user to be monitored,
wherein each detecting device of the plurality of detecting devices is configured to transmit to said remote management entity:
the identification code of the detecting device,
a plurality of patch identification codes received,
a plurality of timestamps, each associated with the reception of a patch identification code, and
a plurality of the user's body temperature data each received together with a patch identification code,
wherein the remote management entity is configured to store a detector log for each detecting device, said detector log comprising the identification code of each monitoring patch detected by the detecting device, the corresponding timestamp and the corresponding data of user's body temperature transmitted by the monitoring patch.

8. The system according to claim 7, wherein the remote management entity is configured to:
generate a contact list comprising the patch identification codes included in the detector log of a selected detecting device, wherein the log comprises the patch identification code of a selected monitoring patch; and
include in the contact list a patch identification code included in the detector log of the selected detecting device, only if said patch identification code is associated with a timestamp comprised in a predetermined time interval.

9. The system according to claim 1, wherein each detecting device is connected to a respective blocking element of the at least one corresponding gate and is configured to control a switching thereof between a blocked state, in which the blocking element does not allow transit through the at least one gate, and an unblocked state, in which the blocking element allows transit through the at least one gate, and
wherein each one detecting device is configured to:
detect whether the body temperature data is indicative of a body temperature higher than a threshold value, and if the body temperature measurement is greater than said threshold value, switch or maintain the corresponding blocking element in a blocked state, or if the body temperature measurement is lower than or equal to said threshold value, switch or maintain the corresponding blocking element in the unblocked state.

10. The system according to claim 2, wherein each detecting device is connected to a respective blocking element of the at least one corresponding gate and is configured to control a switching thereof between a blocked state, in which the blocking element does not allow transit through the at least one gate, and an unblocked state, in which the blocking element allows transit through the at least one gate, and wherein each one detecting device is configured to:
check for the presence of a received patch identification code within a list of patch identification codes, and if the received patch identification is comprised in the list, switch or maintain the blocking element in the blocked state, or if the received patch identification is not comprised in the list, switch or maintain the blocking element in the unblocked state; and/or determine a number of users equipped with a monitoring patch who have entered a sub-area of said plurality of sub-areas through the at least one gate, and in case the determined number of users is equal to a threshold value, switch or maintain the blocking element in the blocked state to prevent the entry of further users in said sub-area.

11. The system according to claim 1, wherein at least a part of the transceiver module, of the memory module, of the sensor and/or of a circuitry of the monitoring patch is configured to alter its operation in response to the removal of the monitoring patch from the epidermis of the user to be monitored.

12. The system according to claim 11, wherein the transceiver module comprises a portion configured to break when the monitoring patch is removed from the epidermis of the user to be monitored.

13. The system according to claim 12, wherein the monitoring patch comprises a support substrate comprising at least one pre-cut portion so as to define a corresponding break line, which causes a division into at least two parts of the support during removal of the monitoring patch from the user's skin, and, wherein a portion of the transceiver module is made by means of a film of conductive material applied over said pre-cut portion of the support substrate said portion of the transceiver module being configured to break during division into at least two parts of the support caused by removal of the patch.

14. A method for monitoring the condition and movements of at least one user, the method comprising the steps of:

applying at least one adhesive monitoring device for skin application or at least one monitoring patch, on the epidermis of the user to be monitored, said at least one patch comprising an adhesive substrate for skin use in which are embedded or to which are bound at least:
a sensor configured to detect a body temperature of the user,
a memory module, configured to store data, and
a transceiver module;

by a detecting device arranged in correspondence with a gate, detecting presence of the at least one monitoring patch within a predetermined distance with respect to a gate associated with a sub-area of a plurality of sub-areas, the plurality of sub-areas defining a monitoring area, activating a communication channel between the at least one detecting device and the at least one detected monitoring patch to receive at least one temperature data detected by the user's body temperature sensor;

transmitting to the at least one detected monitoring patch a detector identification code associated with the at least one detecting device and a corresponding timestamp, and storing in the memory module of the at least one monitoring patch each identification code of the detecting device and each corresponding timestamp received.

15. The method according to claim 14, further comprising the steps of:

by at least one monitoring patch, transmitting a patch identification code, and by the detecting device, storing the patch identification code of the at least one monitoring patch, the user's body temperature measurement provided by the at least one monitoring patch and a timestamp associated with the reception of the patch identification code.

* * * * *